(12) United States Patent
Jessop

(10) Patent No.: US 7,879,002 B2
(45) Date of Patent: Feb. 1, 2011

(54) MIXING DEVICE INCLUDING A PLUNGING MIXING MEMBER FOR USE WITH A SYRINGE

(75) Inventor: Neil T. Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 25 days.

(21) Appl. No.: 12/258,746

(22) Filed: Oct. 27, 2008

(65) Prior Publication Data

US 2009/0112157 A1    Apr. 30, 2009

Related U.S. Application Data

(60) Provisional application No. 60/984,078, filed on Oct. 31, 2007.

(51) Int. Cl.
*A61M 37/00* (2006.01)

(52) U.S. Cl. .............................. 604/91; 604/82; 604/90; 366/255

(58) Field of Classification Search .................... 604/91, 604/82, 90; 366/130, 255
See application file for complete search history.

(56) References Cited

U.S. PATENT DOCUMENTS

| | | | | |
|---|---|---|---|---|
| 3,370,754 | A | * | 2/1968 | Cook et al. .................. 222/132 |
| 4,159,570 | A | | 7/1979 | Baskas et al. |
| 4,208,133 | A | * | 6/1980 | Korte-Jungermann ....... 366/130 |
| 4,966,468 | A | | 10/1990 | Bruning |
| 5,041,088 | A | * | 8/1991 | Ritson et al. .................. 604/88 |
| 5,286,257 | A | * | 2/1994 | Fischer ......................... 604/82 |
| 5,328,462 | A | | 7/1994 | Fischer |
| 5,551,778 | A | | 9/1996 | Hauke et al. |
| 5,569,193 | A | * | 10/1996 | Hofstetter et al. ............. 604/89 |
| 5,643,206 | A | | 7/1997 | Fischer |
| 5,665,066 | A | | 9/1997 | Fischer |
| 5,697,903 | A | | 12/1997 | Fischer |
| 5,908,054 | A | | 6/1999 | Safabash et al. |
| 5,957,166 | A | | 9/1999 | Safabash |
| 6,234,190 | B1 | | 5/2001 | Fischer et al. |
| 6,309,372 | B1 | | 10/2001 | Fischer et al. |
| 6,592,251 | B2 | | 7/2003 | Edwards et al. |
| 6,921,380 | B1 | | 7/2005 | Epstein et al. |

(Continued)

FOREIGN PATENT DOCUMENTS

JP    2005-186026    7/2005

(Continued)

*Primary Examiner*—Nicholas D Lucchesi
*Assistant Examiner*—Brooke M Matney
(74) *Attorney, Agent, or Firm*—Workman Nydegger

(57) ABSTRACT

Mixing devices used with a syringe or syringe system and related systems for mixing dissimilar components contained therein. The devices and systems include a hollow elongate handle having a proximal end, a distal delivery end, and a delivery passageway therethrough. A mixing member is disposed at or near the proximal end of the hollow elongate handle, which mixing member and a portion of the handle are axially slidable within a syringe barrel during use. The user may push and pull the distal end of the handle, causing corresponding axial movement of the mixing member within the syringe barrel. The devices and systems may be used to homogenously mix difficult to mix two part compositions, as well as single part compositions which include components that may tend to separate over time (e.g., a fluoride varnish composition).

26 Claims, 12 Drawing Sheets

U.S. PATENT DOCUMENTS

| | | |
|---|---|---|
| 7,168,847 B2 | 1/2007 | Frei et al. |
| 7,195,615 B2 * | 3/2007 | Tan .......................... 604/171 |
| 2001/0016703 A1 | 8/2001 | Wironen et al. |
| 2001/0037091 A1 | 11/2001 | Wironen et al. |
| 2004/0122359 A1 | 6/2004 | Wenz et al. |
| 2005/0105385 A1 | 5/2005 | McGill et al. |
| 2007/0005075 A1 | 1/2007 | Bogert et al. |
| 2007/0183986 A1 | 8/2007 | Allred et al. |

FOREIGN PATENT DOCUMENTS

| | | |
|---|---|---|
| WO | WO 99/65597 | 12/1999 |

* cited by examiner

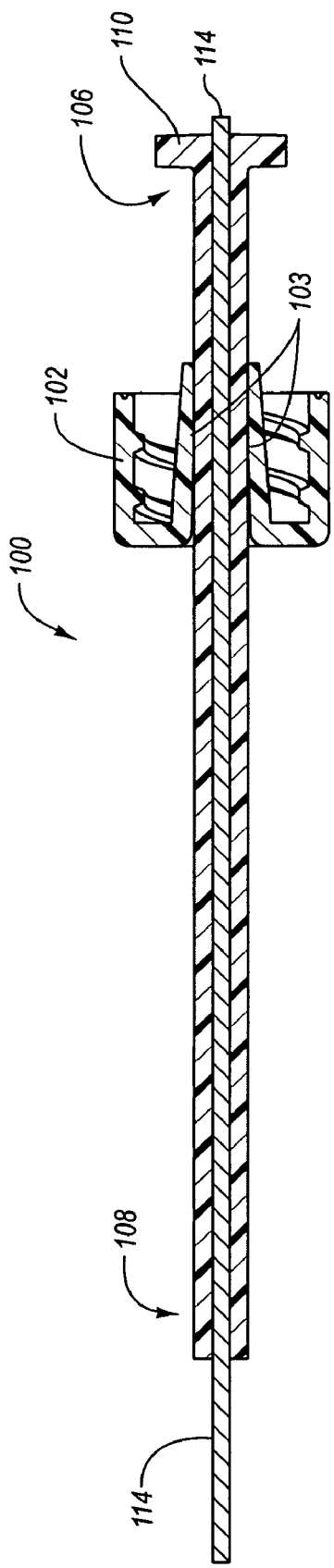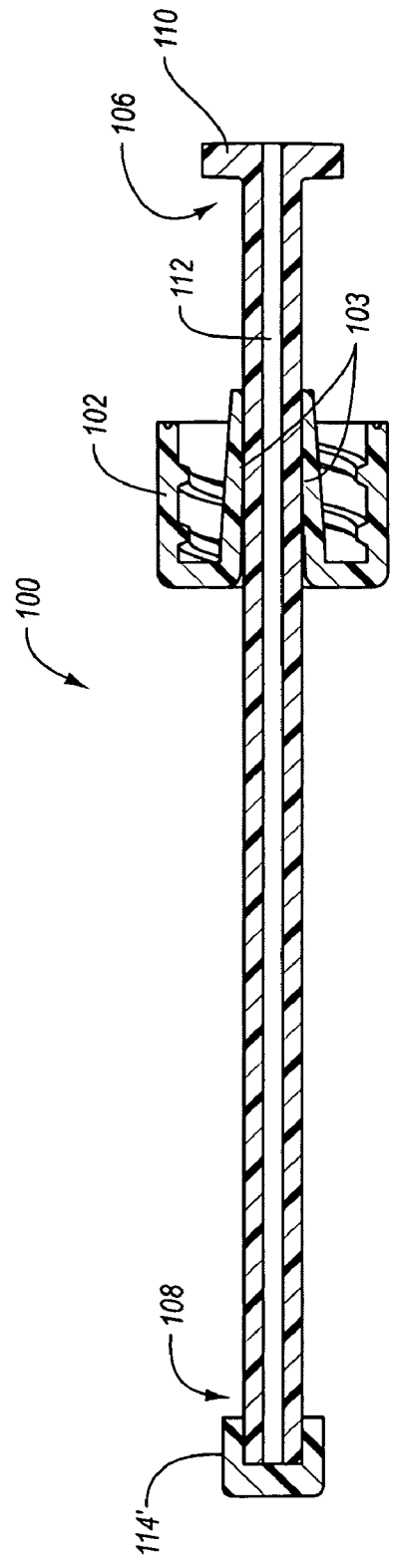
Fig. 2A
Fig. 2B

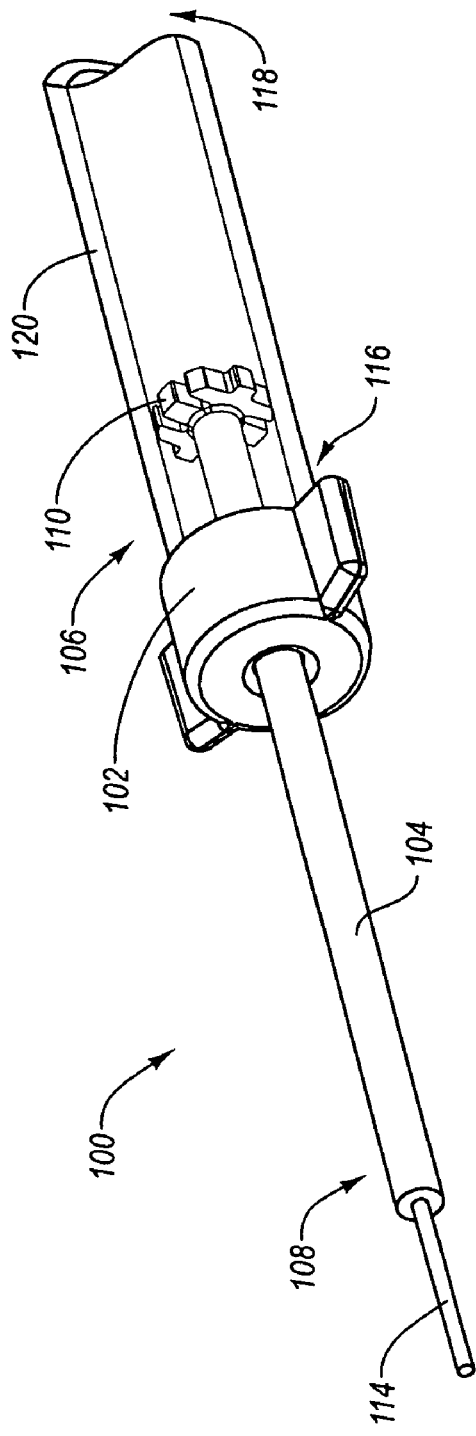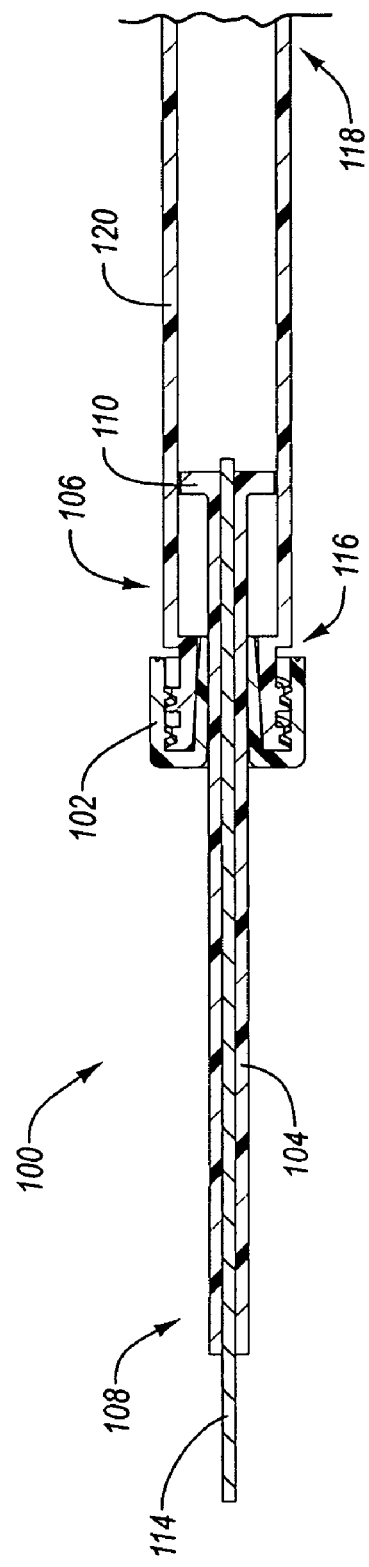
Fig. 3A
Fig. 3B

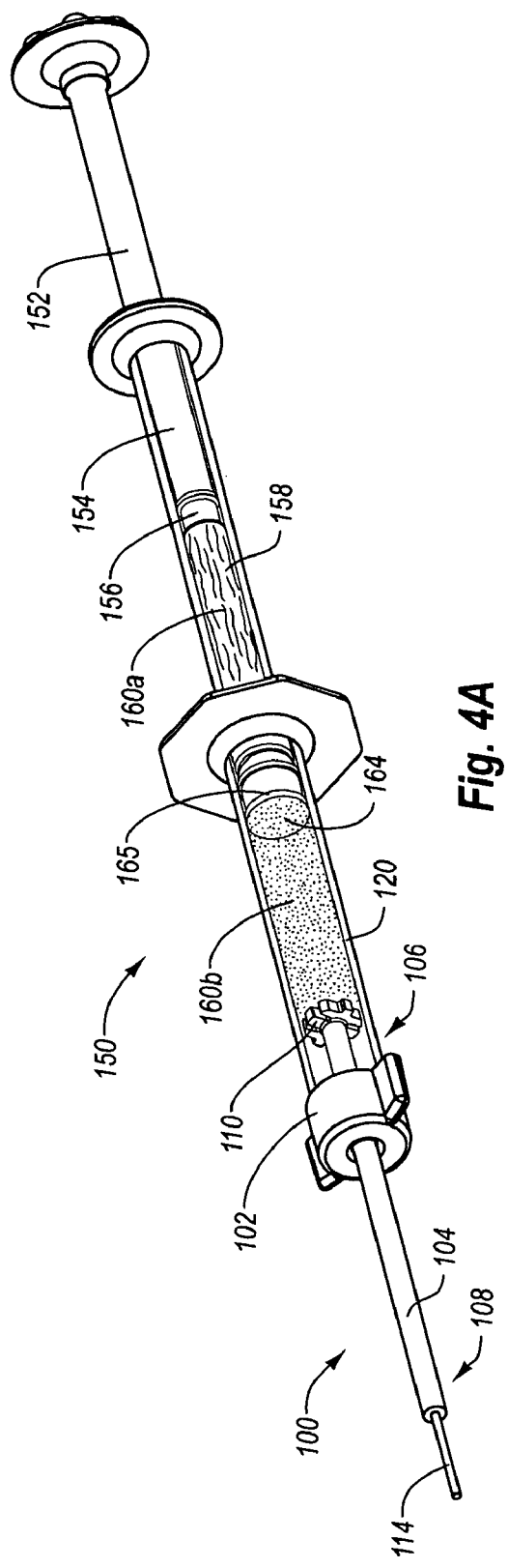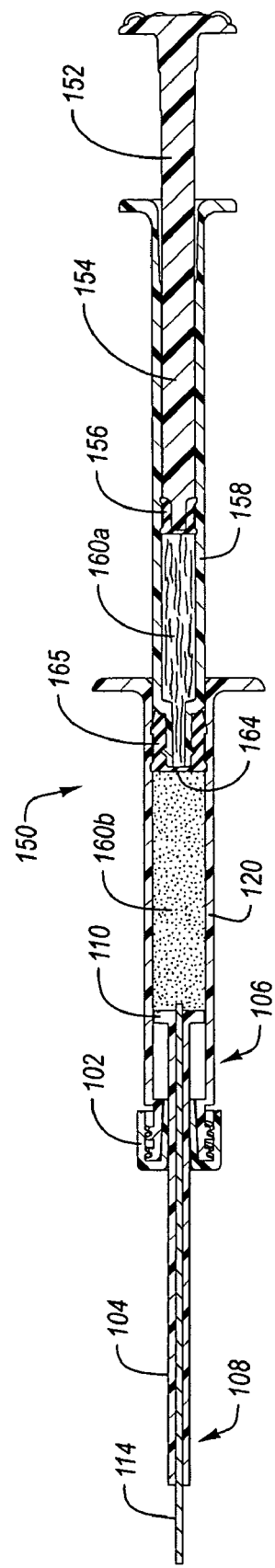
Fig. 4A
Fig. 4B

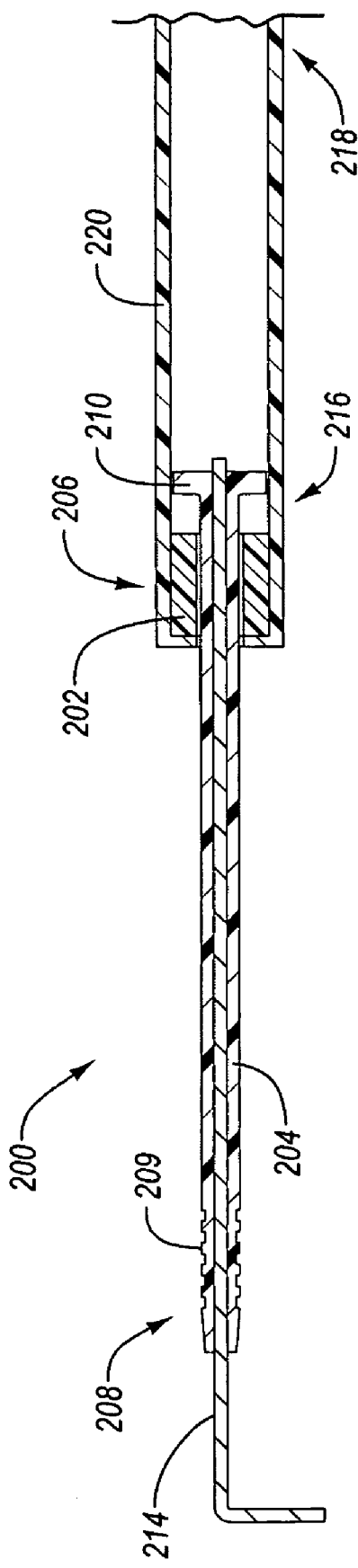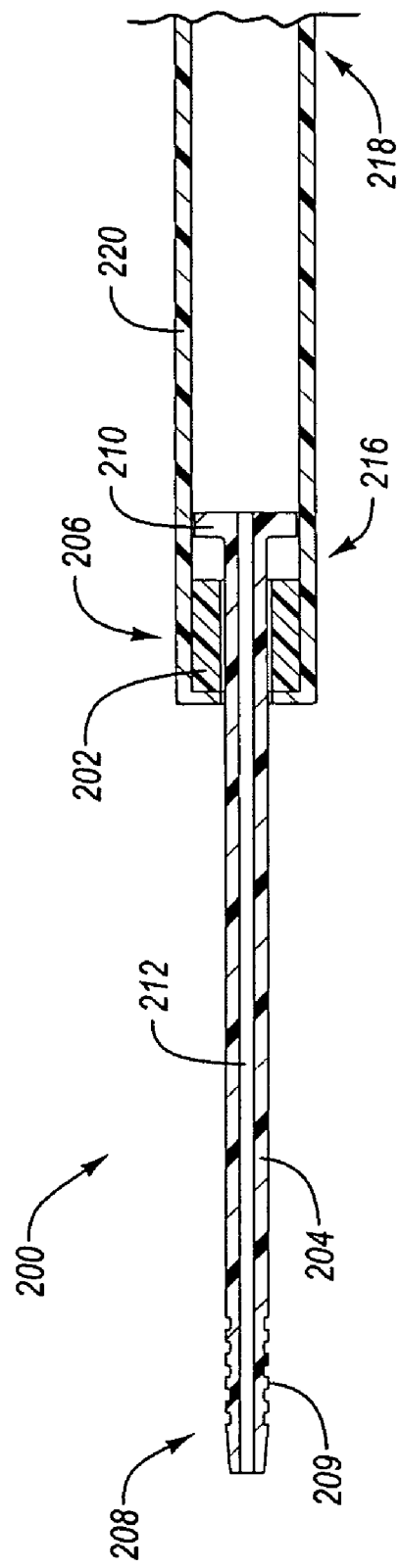

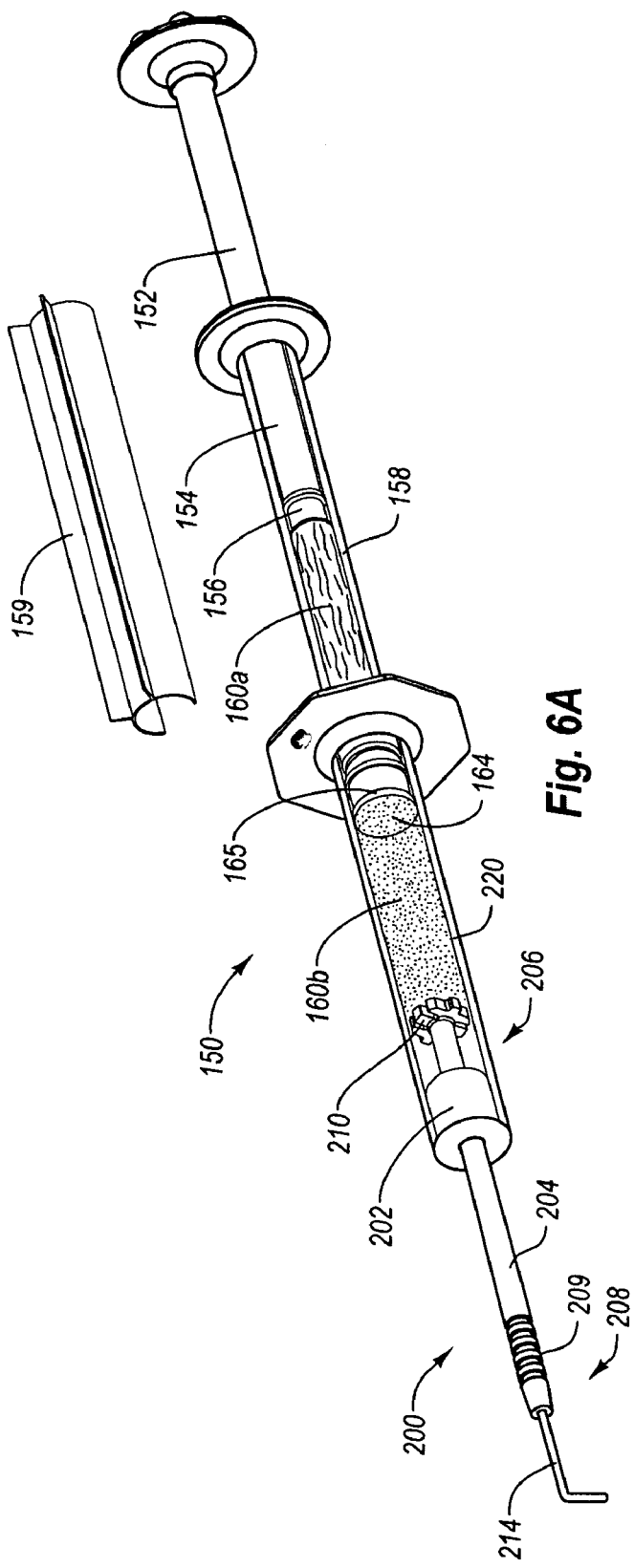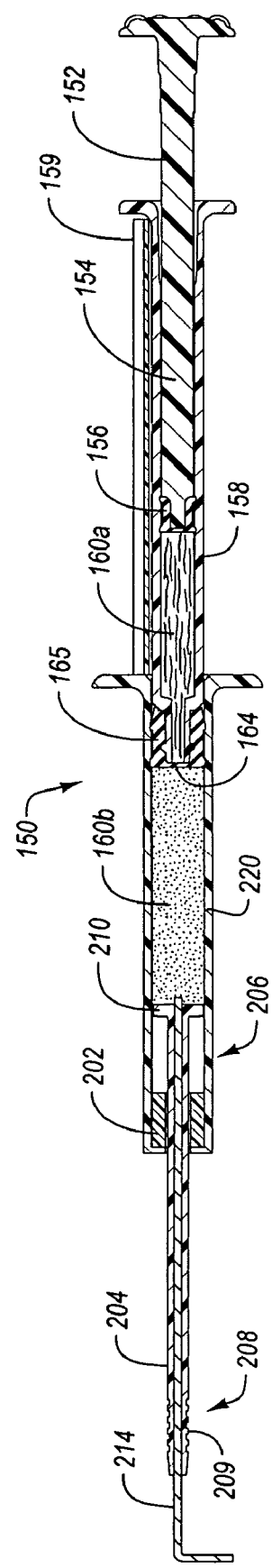
Fig. 6A
Fig. 6B

MIXING DEVICE INCLUDING A PLUNGING MIXING MEMBER FOR USE WITH A SYRINGE

RELATED APPLICATION

The present application claims the benefit of U.S. Patent Application Ser. No. 60/984,078, filed Oct. 31, 2007, entitled "MIXING DEVICE INCLUDING A PLUNGING MIXING MEMBER FOR USE WITH A SYRINGE", the disclosure of which is incorporated by reference in its entirety.

BACKGROUND OF THE INVENTION

1. The Field of the Invention

The present application is directed to devices and related systems for storing, mixing, and dispensing compositions requiring mixing by the user prior to being dispensed (e.g., two-part dental compositions).

2. The Relevant Technology

Many modern formulations are multipart compositions packaged in two parts, often known as A and B components. Upon mixing, the A and B components typically undergo a chemical reaction which causes the resultant composition to "set up" or "cure" in some desired manner. In the dental field, for example, several two-part formulations currently enjoy wide use, such as glass ionomer cements and resinous luting cements. Dental impression materials are also typically made using A and B components.

In order to function properly, it is important that the A and B components of two-component systems be mixed together rapidly and thoroughly and in the right proportions. Failure to rapidly mix the components can result in loss of valuable working time with the resultant composition, and can impact the ability to obtain a thorough mix as the composition may begin to set up unevenly. Failure to mix thoroughly can result in a composition having less than optimum characteristics. For example, if a poorly mixed composition is used as a cement, it is possible that portions of the cement will fail to reach the chemical strength required for a long-term bond.

Problems of obtaining rapid and uniform mixing are often complicated by physical and/or chemical differences in the A and B components. It is often necessary to mix two liquids, while other times it is necessary to mix a powder with a liquid, or two pastes together. Sometimes there are equal amounts of the A and B components, but in other cases there is more of one component than another. Additionally, the two components may have similar viscosities or widely differing viscosities. Components having greatly differing viscosities or other physical or chemical properties are typically harder to mix than components having similar physical or chemical properties.

One method employed for mixing multiple components has been simple mechanical mixing, through the use of a mixing bowl or pad and a stir instrument such as a spatula. This method can be messy and time consuming. It may also be difficult to determine whether mixing is sufficiently thorough.

An alternative and generally superior system uses two syringes, and optionally a coupler between the two syringes. The distal end of each syringe is coupled to the coupler or directly to the other syringe. The components may be passed back and forth between the syringes in order to mix the components.

BRIEF SUMMARY OF THE PREFERRED EMBODIMENTS

The present invention is directed to mixing devices for use with a syringe or syringe system. The mixing device includes a hollow elongate handle having a proximal end, a distal delivery end, and an axial delivery channel extending therebetween. The distal delivery end of the channel is initially closed. A mixing member is disposed at or near the proximal end of the hollow elongate handle, and an annular coupling ring for coupling the device to a syringe barrel is axially slidably disposed about the hollow elongate handle between the proximal and distal ends of the handle so that the handle is able to slide axially within the coupling ring. In one embodiment, the coupling ring is configured with a thread and groove type coupling structure for coupling to a distal end of a syringe barrel, which may include complementary coupling structure.

When the mixing device is coupled to a syringe barrel, the mixing member is disposed within the syringe barrel and may be pushed and pulled up and down within the barrel as the user grasps the distal end of the elongate handle, pushing and pulling the handle so as to cause a corresponding axial movement of the mixing member within the syringe barrel. The movement of the mixing member within the syringe barrel acts to homogenously mix the composition and to break up any bubbles present. The device may be used to mix two part compositions as described above (e.g., glass ionomer cements, composites, sealants, etc.) as well as one-part compositions which include components which may tend to separate over time (e.g., a fluoride varnish composition including a fluoride salt in which the salt tends to settle out of the carrier over time), where it may be necessary to remix the composition prior to application.

A related embodiment is directed to a syringe mixing system including a plunger comprising an elongate stem and a plug at a distal end thereof, a syringe barrel for containing a composition where the plunger is slidably received within the syringe barrel, a hollow elongate handle including proximal and distal ends and an axial delivery channel therebetween, in which the handle is slidably disposed through a distal end of the syringe barrel (with or without the aid of an annular coupling ring), and a mixing member disposed at or near the proximal end of the hollow elongate handle so that the mixing member is axially slidable within the syringe barrel so as to allow a user to mix the composition prior to dispensing the composition.

The hollow elongate handle is advantageously initially closed so as to prevent the composition from prematurely entering the distal delivery end of the delivery channel. A removable cap may be fitted over the distal delivery end of the hollow handle, or preferably, the hollow elongate handle is initially provided with a removable plug inserted within the distal delivery end of the hollow elongate handle. Preferably, the removable plug has a length at least as long as the handle so as to at least partially fill the length of the channel within the hollow elongate handle, e.g., so that both ends (both the distal delivery end and the proximal end adjacent the mixing member) are initially plugged. A portion of the plug may advantageously extend out the distal delivery end. Once mixing is complete and it is desired to dispense the composition, the plug may be pulled out the distal delivery end, allowing the composition to be dispensed through the hollow elongate handle.

In another aspect, the invention is directed to a syringe-in-syringe mixing system for mixing a two-part composition. Such a system includes a first inner plunger, a hollow outer plunger for containing a first component, wherein the hollow outer plunger is initially closed at its distal end, and a syringe barrel for containing a second component that is initially separate from the first component. The inner plunger is slidably received within the hollow inner plunger, and the hollow outer plunger is itself slidably received within the syringe barrel, acting as the main plunger for the syringe barrel. The system further includes a hollow elongate handle having a proximal end, a distal end, an axial delivery channel therethrough. A mixing member is attached to the proximal end of the handle so as to be slidably disposed within the distal end of the syringe barrel.

The mixing member may be used to mix the two components of the composition together after the first inner plunger is pressed, forcing the first component into the syringe barrel containing the second component. The mixing member is particularly useful for mixing two components which may not readily mix together simply as a result of turbulence caused by introducing the first component into the syringe barrel with the second component (e.g., compositions in which at least one component is highly viscous, powder-liquid compositions, and/or compositions including at least one paste component).

The foregoing mixing devices have been found to be less bulky and easier to use compared to prior syringe mixing systems. They can eliminate the need for a second syringe used only for mixing. They can also reduce or eliminate formation of bubbles in the mixed composition.

These and other advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 2A is a cross-sectional view of the mixing device of FIG. 1;

FIG. 2B is a cross-sectional view of an alternative mixing device including a removable cap rather than a removable plug;

FIG. 3A is a perspective view of a mixing system including a mixing device similar to that illustrated in FIG. 1 coupled with a syringe barrel;

FIG. 3B is a cross-sectional view of the mixing system of FIG. 3A;

FIG. 4A is a perspective view of an exemplary syringe-in-syringe mixing system incorporating a mixing member with a hollow elongate handle;

FIG. 4B is a cross-sectional view of the syringe-in-syringe mixing system of FIG. 4A;

FIG. 5B is a cross-sectional view of the syringe mixing device of FIG. 5A;

FIG. 5C is a cross-sectional view of the syringe mixing device of FIG. 5B, with the removable plug removed;

FIG. 6A is a perspective view of another exemplary syringe-in-syringe mixing system incorporating the syringe mixing device of FIGS. 5A-5C;

FIG. 6B is a cross-sectional view of the syringe-in-syringe mixing system of FIG. 6A;

DETAILED DESCRIPTION OF THE PREFERRED EMBODIMENTS

I. Introduction

The present invention is directed to mixing devices for use with a syringe barrel, a syringe-in-syringe system, and related systems. The devices and systems include a hollow elongate handle having a proximal end, a distal delivery end, and a delivery channel therebetween, in which the distal delivery end of the channel is initially closed. A mixing member is disposed at or near the proximal end of the hollow elongate handle. The device may be configured for coupling with a syringe barrel (e.g., with an annular coupling ring), or may be formed or assembled so that the mixing member and a portion of the handle are axially slidable within the distal end of the syringe barrel (e.g., without an annular coupling ring, but with a sealing ring within the distal end of the syringe barrel where the handle is axially slidable through a passageway through the sealing ring).

In use, the user may push and pull the distal end of the hollow elongate handle, causing a corresponding axial cycling of the mixing member within the syringe barrel. The devices and systems may be used to mix two part compositions, as well as single part compositions which include components that may tend to separate over time (e.g., a fluoride varnish composition). The mixing member is particularly useful for mixing together components which may otherwise be difficult to mix together (e.g., compositions in which at least one component is highly viscous, powder-liquid compositions, and/or compositions including at least one component having a paste like consistency)

II. Exemplary Mixing Devices and Systems

Figure 1:
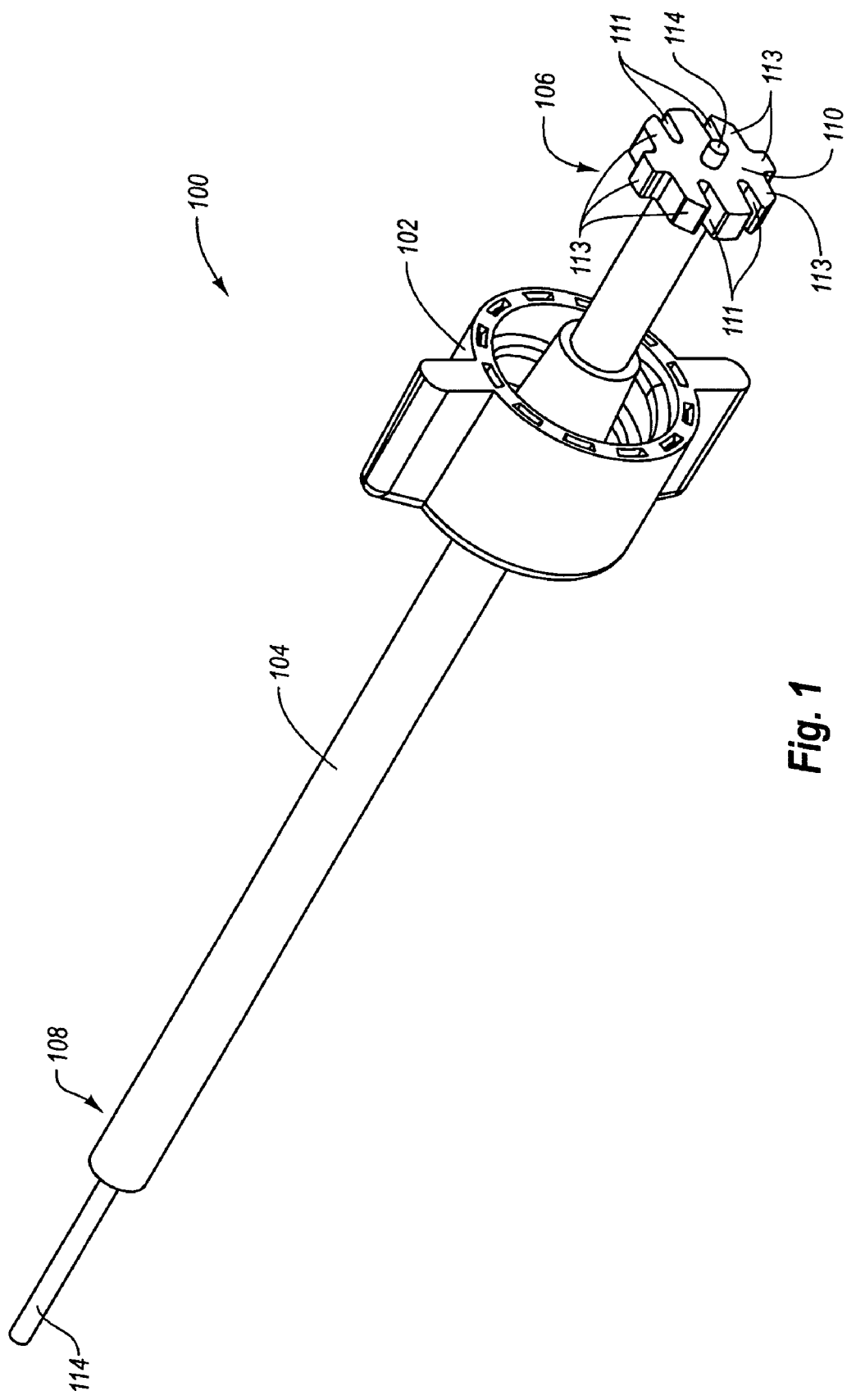
FIG. 1 is a perspective view of an exemplary mixing device configured for coupling to a syringe.
Figure 2C:
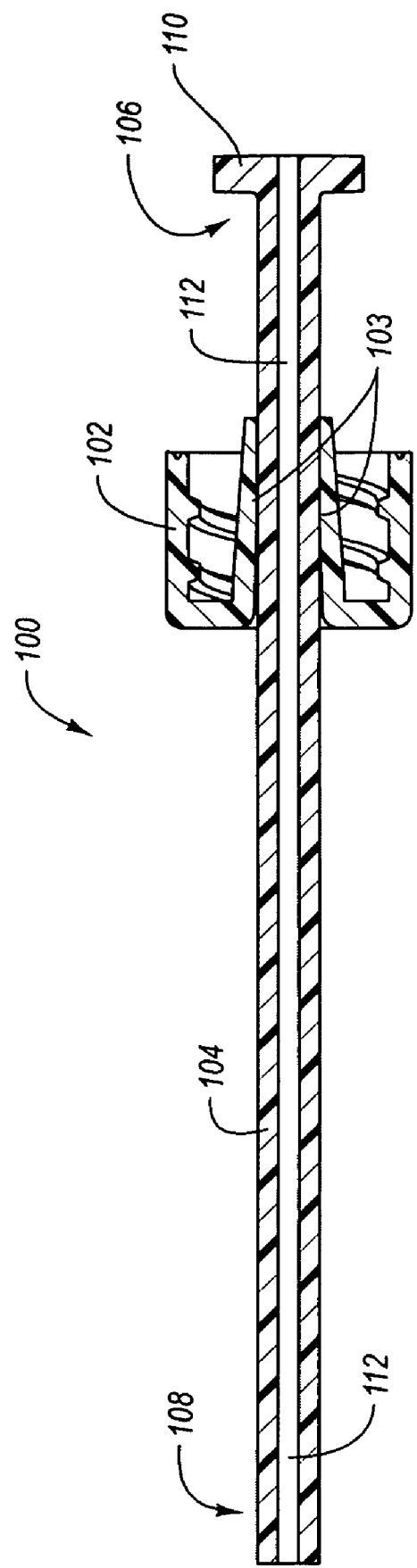
FIG. 2C is a cross-sectional view of the mixing device of FIG. 1 with the removable plug removed.

FIGS. 1-2C illustrate an exemplary mixing device 100 including an annular coupling ring 102 with a central passageway, a hollow elongate handle 104 received through the central passageway of annular coupling ring 102 and having a proximal end 106 and a distal delivery end 108, and a mixing member 110 disposed at or near proximal end 106 of handle 104. As shown in FIGS. 2B-2C, hollow elongate handle 104 includes a centrally disposed axial delivery channel 112 along the length of the handle 104, which allows for passage of a mixed composition so that the composition may be dispensed out the distal delivery end 108. It will be appreciated that delivery channel 112 may extend part or along the entire length of handle 104 (e.g., with an end hole and/or side hole(s) through handle 104. As seen in FIGS. 1, 2A and 2B, channel 112 is advantageously initially closed. In the example illustrated in FIGS. 1 and 2A, a removable plug 114 is received within delivery channel 112, blocking both the proximal and distal ends 106 and 108 (and the full length of delivery channel 112 therebetween) of hollow elongate handle 104. In the illustrated embodiment, plug 114 extends beyond both proximal end 106 and distal delivery end 108. Extension beyond distal delivery end 108 advantageously provides a portion of plug 114 that may be gripped and pulled by the practitioner when it is desired to remove plug 114. Extension of plug 114 at least to and/or beyond proximal end 106 is helpful so as to avoid plugging of delivery channel 112 (e.g., with dry powder). Alternatively, as illustrated in FIG. 2B, the distal delivery end 108 of delivery channel 112 may be initially closed by use of a removable cap 114' positioned over end 108.

Mixing member 110 may advantageously be configured so as to have a substantially circular cross-section (transverse to a longitudinal axis of hollow elongate handle 104). As perhaps best seen in FIG. 1, mixing member 110 may include a plurality of channels 111 formed through the substantially circular cross-section so as to define a plurality of outwardly extending paddles 113 between channels 111. The maximum outer diameter of mixing member 110 may be sized so that paddles 113 are configured to wipe against an interior side wall of a coupled syringe (FIGS. 3A-3B). Such a configuration of mixing member 110 aids in breaking up gas bubbles (including air bubbles) and in mixing the composition, as the components are able to turbulently flow between paddles 113 in channels 111 as mixing member 110 slides axially up and down within the syringe barrel, together with wiping action by paddles 113, which induces good and efficient mixing.

Plug 114 and handle 104 may be formed of any suitable materials. In one example, removable plug 114 may be formed with hollow elongate handle 104 as a two-shot molded system where plug 114 may comprise a relatively soft elastomer (e.g., having a shore A durometer hardness not greater than about 50, more preferably not greater than about 40, most preferably not greater than about 30) as compared to handle 104 (which may be formed of a harder plastic or other material). Such a configuration allows plug 114 to form a tight seal against the interior of handle 104, sealing off delivery channel 112 until plug 114 is removed. In another example, plug 114 may be of a more rigid thermoplastic (or even metal), while the handle 104 can be formed of a relatively soft, somewhat flexible material (e.g., polyethylene and/or polypropylene). In either case, the difference in material properties between the plug 114 and hollow handle 104 advantageously allows plug 114 to be easily pulled out of delivery channel 112, while also providing a good seal prior to removal.

Annular coupling ring 102 may include raised threads and/or recessed grooves so as to allow coupling ring 102 to be coupled with a syringe barrel. Any coupling mechanism known in the art may be used, the illustrated luer type thread and groove coupling mechanism being an example. Other coupling mechanisms for coupling the mixing device with a syringe or syringe system will be apparent to one skilled in the art. Annular coupling ring 102 and hollow elongate handle 104 are axially slidable relative to one another. Handle 104 (e.g., near distal end 108) may be grasped by the user and pushed or pulled so as to cause handle 104 to slide within ring 102. Because proximal end 106 contacts the components within a syringe barrel during use, it is preferable that a seal be provided between annular coupling ring 102 and elongate hollow handle 104 so as to prevent the composition from entering into any space between ring 102 and handle 104. According to one embodiment, a seal may be provided by forming one or more of the contacting portions of ring 102 and/or handle 104 of a flexible, self-sealing material that will tend to seal against the opposite surface as ring 102 and handle 104 slide relative to one another. For example, surface 103 of ring 102 may be formed of a thermoplastic elastomer or similar material so as to seal against the outer surface of handle 104, preventing entrance of the composition into the sealed area from proximal direction 106 as handle 104 slides within ring 102. Alternatively, all or a portion of the exterior surface of handle 104 could be formed of such a thermoplastic elastomer or similar elastomeric material so as to seal against surface 103 of ring 102. According to another embodiment, both the exterior surface of handle 104 and surface 103 may be formed of a thermoplastic elastomer or similar elastomeric material.

FIGS. 3A and 3B illustrate perspective and cross-sectional views, respectively, of the mixing device 100 coupled to the distal end 116 of a syringe barrel 120. Depending on the configuration and relative sizes (i.e., diameter) of mixing member 110 and the opening of syringe barrel 120 at distal end 116, it may be necessary to separate hollow elongate handle 104 from coupling ring 102 and insert the distal delivery end 108 of handle 104 a through proximal end 118 of syringe barrel 120, and continuing insertion until handle 104 extends through (i.e., distally) annular coupling ring 102. Alternatively, if the opening into syringe barrel 120 at distal end 116 is sufficiently large as to allow passage of mixing member 110, it may not be necessary to separate handle 104 from coupling ring 102, but to simply insert mixing member 110 and the proximal end 106 of handle 104 through the distal end 116 of syringe barrel 120.

Syringe barrel 120 is illustrated as one example of a syringe or syringe system to which the system may be coupled. Of course, it may also be possible to form a syringe system similar to that illustrated in FIGS. 3A-3B in which the hollow elongate handle 104 is coupled to syringe barrel 120 without a coupling ring. For example, one such embodiment may include a syringe barrel, a hollow elongate handle with a mixing member at or near a proximal end thereof where the hollow elongate handle is axially slidably disposed within the distal end 116 of syringe barrel 120. In other words, such an embodiment may not include a coupling ring 102, but instead the elongate handle 104 is simply pinched between the sides of the opening at the distal end 116 of syringe barrel 120. A seal may be maintained between the exterior surface of handle 104 and the inside surfaces surrounding the opening at the distal end 116 in a similar manner as described above relative to the seal between handle 104 and coupling ring 102 (e.g., one or both of the exterior contacting surfaces may include an elastomeric material so as to form a seal against the opposing contact surface). One such example is illustrated and described in conjunction with FIGS. 5A-5C.

FIGS. 4A-4B show mixing device 100 coupled to a syringe-in-syringe system 150. Syringe-in-syringe system 150 includes a first inner plunger 152 comprising an elongate stem 154 and a plug 156 at a distal end of stem 154. First inner plunger 152 is axially slidably received within a hollow outer plunger 158, which hollow plunger 158 is configured to contain a first component 160a (e.g., a liquid). Hollow plunger 158 acts as the main plunger for syringe barrel 120. A second component 160b (e.g., a powder) is initially contained separately within syringe barrel 120. In the illustrated embodiment, first component 160a and second component 160b are initially separated by a rupturable membrane 164 formed integral with sealing plug 165, although other structures (e.g., a valve) for initially separating the first and second components will be apparent to one skilled in the art.

Additional details and examples of syringe-in-syringe and other syringe systems which may be used with the present mixing device are disclosed in U.S. patent application Ser. No. 11/673,334, filed Feb. 9, 2007 and entitled SYRINGE-IN-SYRINGE HOLLOW INNER BARREL/PLUNGER WITH INTEGRAL SEAL AND RUPTURABLE MEMBRANE AND RELATED KITS, SYSTEMS, AND METHODS; U.S. patent application Ser. No. 11/414,964, May 1, 2006 and entitled TIME-INDICATING SYRINGE-IN-SYRINGE MIXING DEVICES AND RELATED METHODS FOR STORING AND DISPENSING TWO-PART DENTAL COMPOSITIONS; U.S. patent application Ser. No. 11/537,883, filed Oct. 2, 2006 and entitled TIME-INDICATING SYRINGE MIXING DEVICES AND RELATED METHODS FOR STORING AND DISPENSING TWO-PART DENTAL COMPOSITIONS; U.S. patent application Ser. No. 11/736,457, filed Apr. 17, 2007 and entitled TIME INDICATING SYRINGE MIXING DEVICES AND RELATED METHODS FOR STORING AND DISPENSING TWO-PART DENTAL COMPOSITIONS; and PCT International Patent Application Serial No. PCT/US2007/067556, filed Apr. 26, 2007 and entitled SYRINGE-IN-SYRINGE HOLLOW INNER BARREL/PLUNGER WITH INTEGRAL SEAL AND RUPTURABLE MEMBRANE, the disclosures of which are hereby incorporated by reference.

Figure 5A:
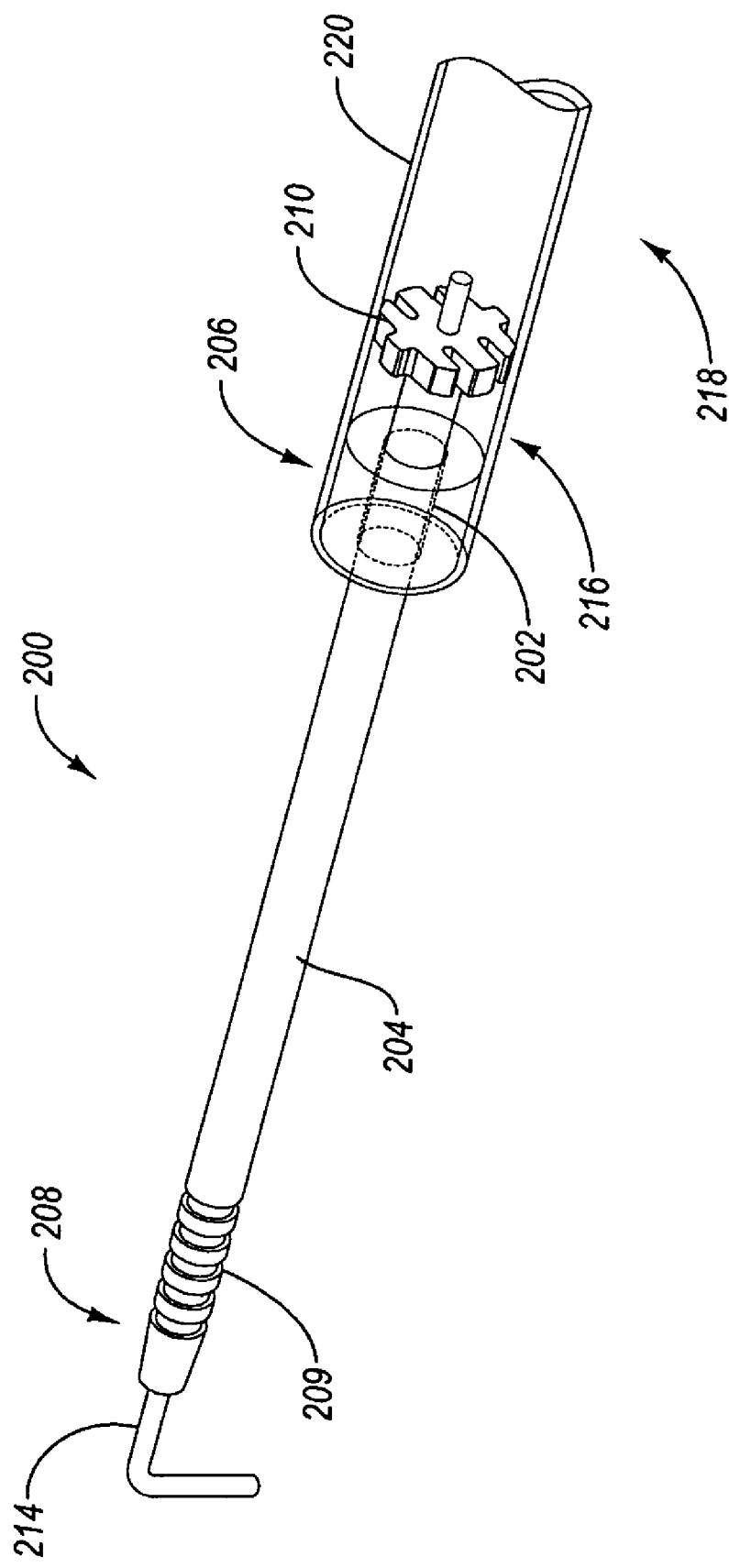
FIG. 5A is a perspective view of an alternative exemplary mixing device without an annular coupling ring, but which includes a sealing ring received within the syringe barrel of the syringe through which the hollow elongate handle is axially slidable.

FIGS. 5A-5C illustrate an alternative syringe system including the mixing device, but without the use of an annular coupling ring. Syringe mixing system 200 includes a hollow elongate handle 204 having a proximal end 206, a distal delivery end 208, an axially disposed delivery channel 212 extending therebetween, and a removable plug 214 initially within channel 212. A mixing member 210 is disposed at or near proximal end 206 of handle 204. Rather than an annular coupling ring that couples to the exterior of the syringe barrel, system 200 includes a sealing ring 202 received at least partially within the distal end of syringe barrel 220. Sealing ring 202 includes a central passageway through which handle 204 is inserted so that sealing ring 202 and hollow elongate handle 204 are axially slidable relative to one another. Handle 204 (e.g., near distal end 208) may be grasped by the user and pushed or pulled so as to slidably cycle handle 204 within ring 202.

Because proximal end 206 contacts the components within syringe barrel 220 during use, it is preferable to provide a seal between sealing ring 202 and elongate hollow handle 204 so as to prevent the composition from entering into any space between sealing ring 202 and handle 204. Such a seal may be provided in a manner as described above with respect to ring 102 and handle 104. Sealing ring 202 may be bonded within syringe barrel 220 (e.g., with an adhesive), or may simply rely on a friction fit between the outer diameter of ring 202 and the inner diameter of syringe barrel 220. Other methods of fixing ring 202 relative to syringe barrel 220 will be apparent to one skilled in the art (e.g., the syringe barrel 220 and sealing ring 220 may be formed integrally as a single piece by injection molding or two-shot molding).

Besides sealing ring 202, system 200 also includes several other differences relative to device 100. Elongate handle 202 includes an articulating portion 209 near its distal end. Such an articulating portion provides additional flexibility at the distal delivery end so that the user may bend the articulating portion 209 to provide an angle for more convenient delivery of the mixed composition. The articulating portion 209 includes alternating spaced apart sections of reduced diameter, which allows the articulating portion 209 to be bent and to hold the angle, as illustrated in FIG. 7D. Removable plug 214 may include a lateral bend (e.g., approximately 90°) near its distal end. Such a bend facilitates easier gripping and selective removal than the straight end plug 114.

According to one method of assembly, hollow elongate handle 204 may initially be be separated from sealing ring 202. Sealing ring 202 is positioned at the distal end of syringe barrel 220 (e.g., by inserting it through proximal end 218), and distal delivery end 108 of handle 104 is inserted through proximal end 218 of syringe barrel 220, continuing insertion until handle 204 extends through (i.e., distally) sealing ring 202 and out the distal end 216 of syringe barrel 216.

FIGS. 6A-6B illustrate a syringe-in-syringe system similar to that of FIGS. 4A-4B, but including the mixing system 200 of FIGS. 5A-5C. Syringe-in-syringe system 150 includes a first inner plunger 152 comprising an elongate stem 154 and a plug 156 at a distal end of stem 154. First plunger 152 is axially slidably received within a hollow outer plunger 158, which hollow plunger 158 is configured to contain a first component 160a (e.g., a liquid). Hollow plunger 158 acts as the main plunger for syringe barrel 220. A second component 160b (e.g., a powder) is initially contained separately within syringe barrel 220. In the illustrated embodiment, first component 160a and second component 160b are initially separated by a rupturable membrane 164 formed integral with sealing plug 165. Sealing ring 202 is disposed at the distal end within syringe barrel 220.

In addition, system 150 is shown with an optional removable safety clip 159 configured to engage with the outside wall of hollow outer plunger 158. Clip 159 has a length approximately equal to (preferably somewhat shorter than) the length of hollow plunger 158, such that it is configured to clip around the plunger 158, preventing plunger 158 from being inserted into syringe barrel 220 before first plunger 152 has been inserted into hollow plunger 158. Such a clip makes it easier for the user to first inject all of the first component into syringe barrel 220 before the hollow outer plunger 158 can be pressed to dispense the composition through the delivery channel of handle 204. In other words, the safety 159 clip prevents premature, or accidental dispensing of the composition. Once the composition has been fully mixed by pushing and pulling to cycle mixing member 210, safety clip 159 may be removed to permit dispensing of the mixed composition from barrel 220.

III. Exemplary Method of Use

Figure 7A:
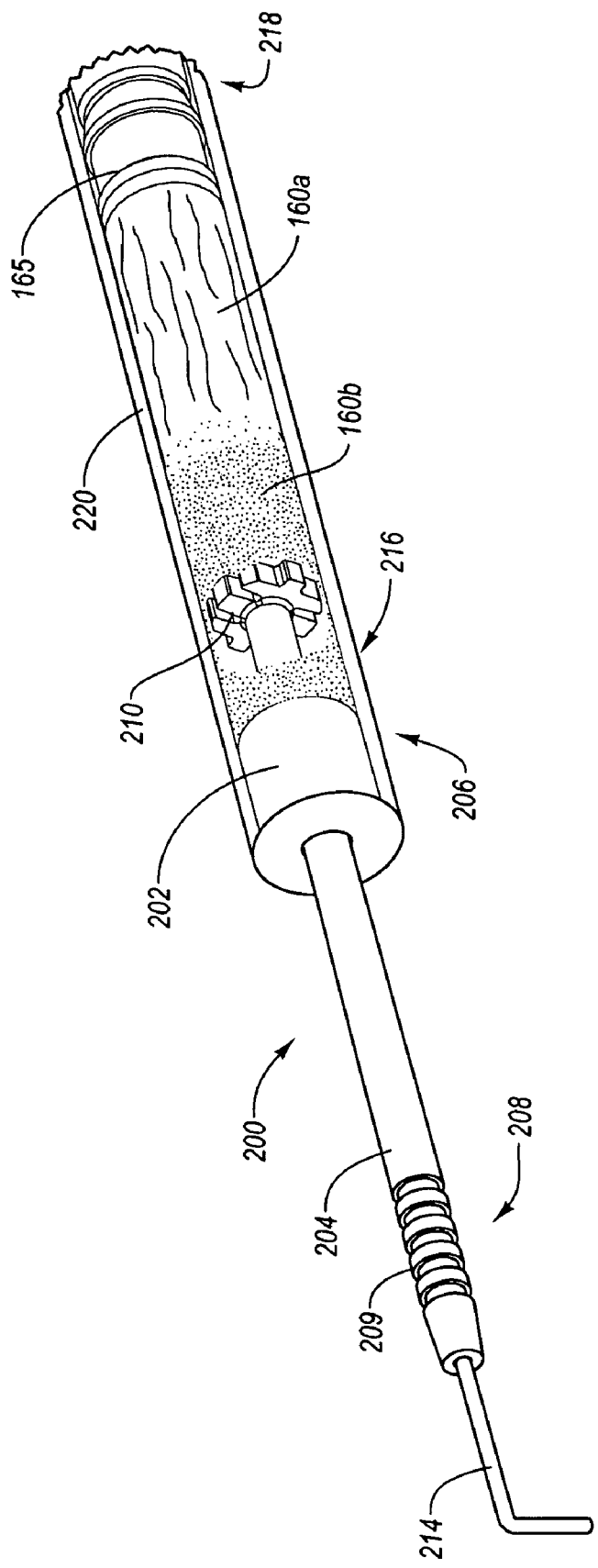
FIG. 7A is a perspective view of the syringe mixing system of FIGS. 6A and 6B in which two components requiring mixing are present within the syringe barrel.
Figure 7B:
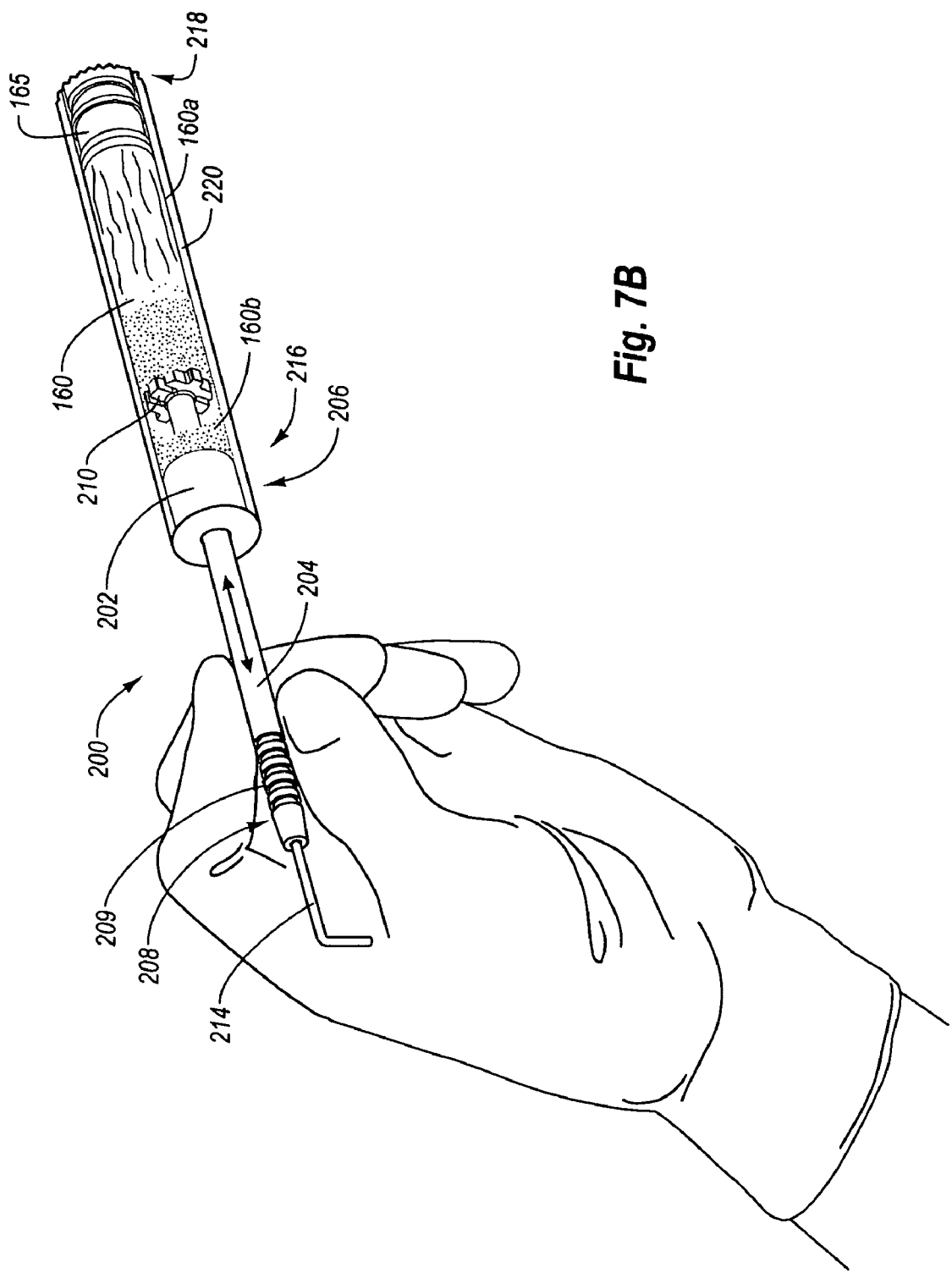
FIG. 7B is a perspective view of the mixing system of FIG. 7A in which a user's hand is grasping a distal portion of the handle to move the handle and thus the mixing member axially so as to mix the two components.
Figure 7C:
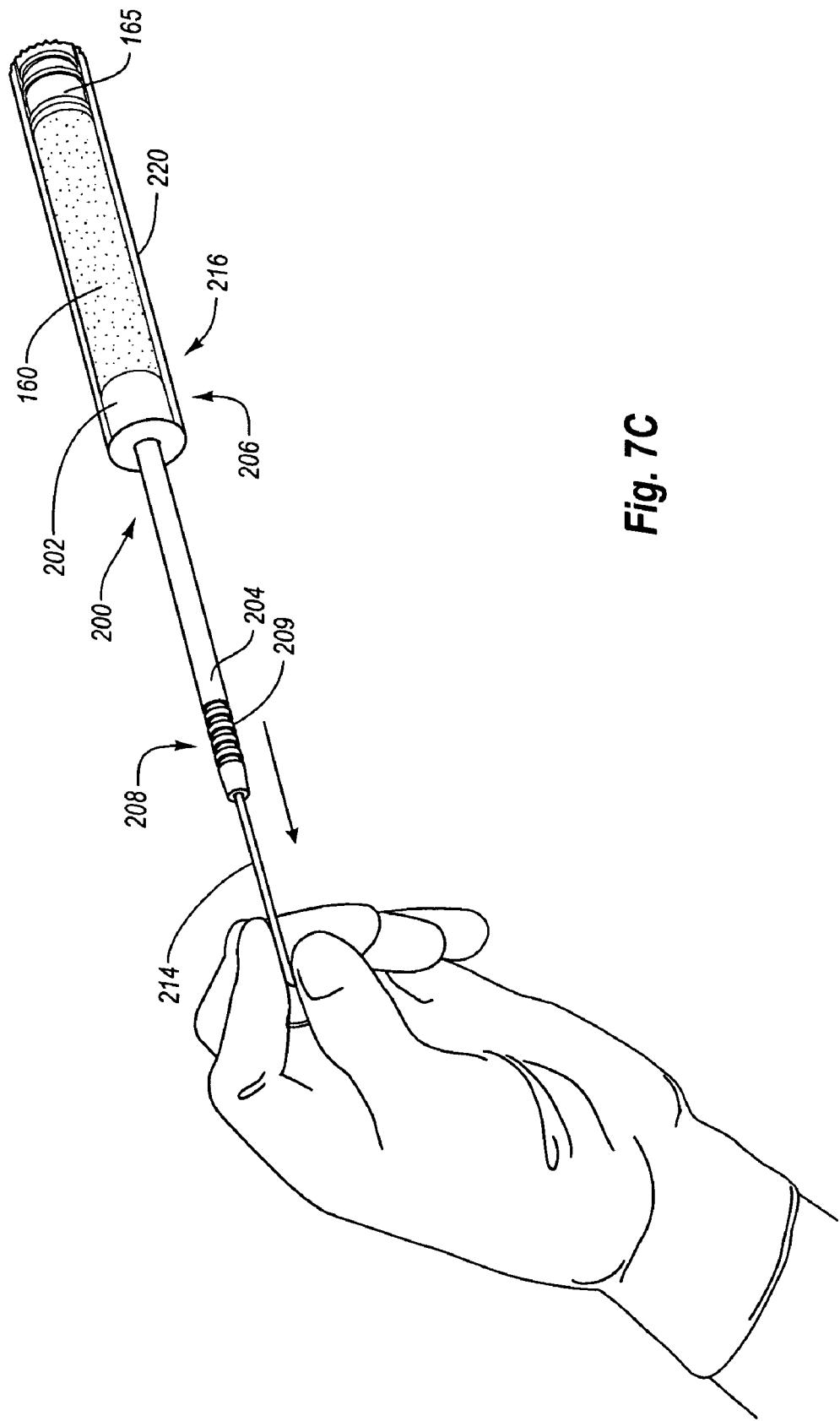
FIG. 7C is a perspective view of the mixing system of FIG. 7B in which the composition has been homogenously mixed and the user is in the act of grasping and pulling the removable plug so as to remove the plug prior to dispensing the mixed composition.
Figure 7D:
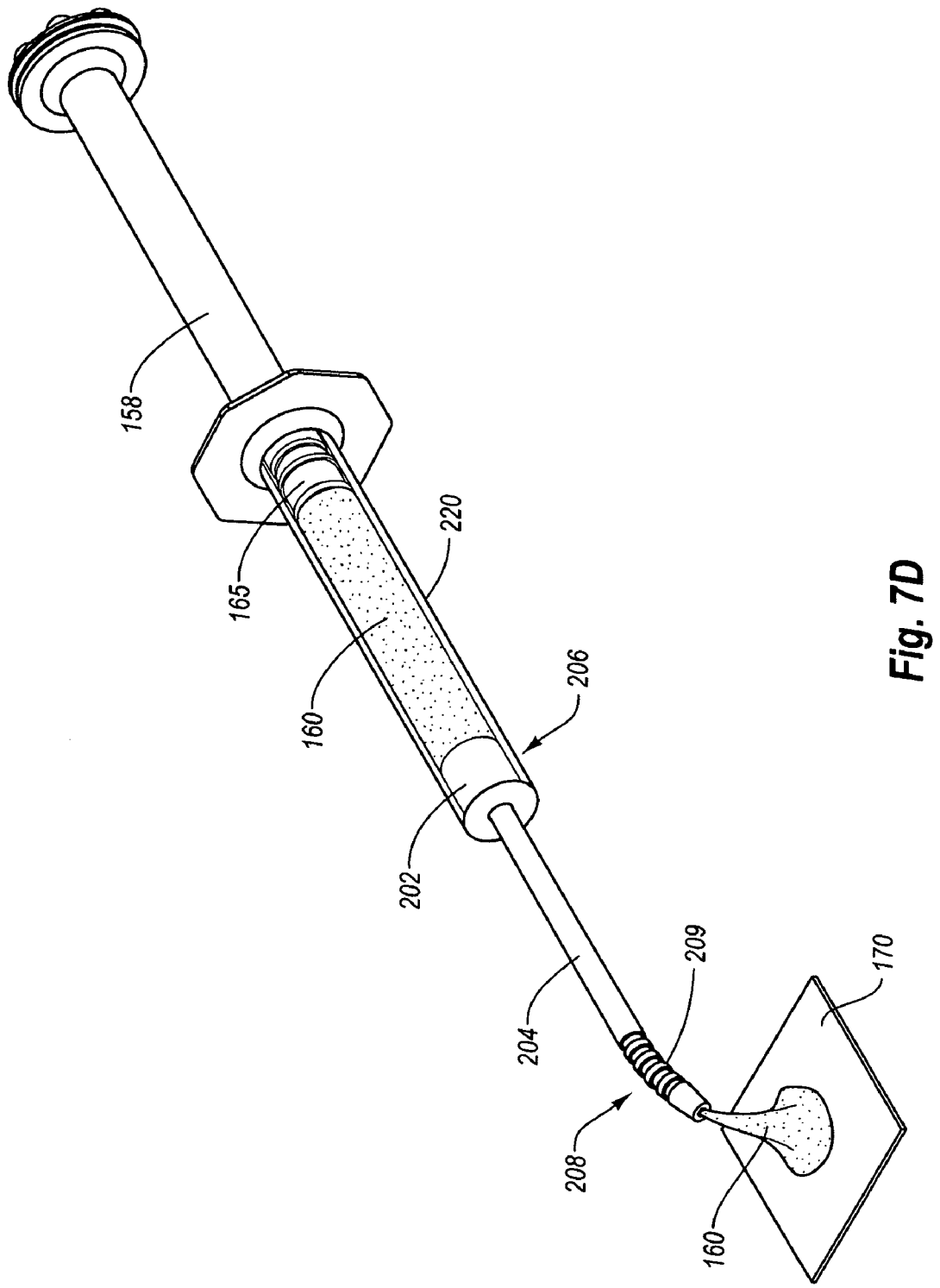
FIG. 7D is a perspective view of the mixing system of FIG. 7C with the plug removed and the composition being dispensed through the distal delivery end of the hollow elongate handle.

FIGS. 7A-7D illustrate system 200 coupled to syringe barrel 220 (which may be connected to the remainder of a syringe-in-syringe system as shown in FIGS. 6A-6B, may be another syringe system, or simply may include a plunger 165 slidably disposed in the proximal end 218 of syringe barrel 220). As seen in FIG. 7A, initially separate components 160a and 160b have been introduced into the same chamber, but are not yet homogenously mixed. Such may particularly be the case with difficult to mix components (e.g., powder-liquid systems, systems including a paste component, or high viscosity liquid systems).

As seen in FIG. 7B, the practitioner may grasp handle 204 near distal delivery end 208 and alternatingly push and pull handle 204. Because handle 204 is slidably disposed through sealing ring 202 and the distal end 216 of syringe barrel 220, pushing and/or pulling of handle 204 results in corresponding axial movement (or cycling) of mixing member 210 within syringe barrel 220 so as to mix first component 160a with second component 160b. Mixing member 210 advantageously allows for simple, fast and substantially homogenous mixing of composition 160, even with powder-liquid compositions, high viscosity compositions and/or compositions including a high viscosity component, and compositions including a component having a paste like consistency in a manner that is clean and very convenient. For example, such a mixing system may be particularly useful in mixing a glass ionomer cement, many of which have the consistency of a paste after mixing or comprise two parts each having a paste like consistency. Other glass-ionomer cements may comprise liquid-liquid systems. In an example of another use, the mixing system may be particularly useful in re-suspending a fluoride salt within a one part fluoride varnish composition just prior to application.

Once the composition 160 has been mixed with mixing member 210 so as to be substantially homogenous, handle 204 may be pulled distally so as to position the proximal end 206 and mixing member 210 at or near the distal end 216 of syringe barrel 220. Such an orientation positions the proximal end of channel 212 (see FIG. 5B) as close as possible to distal end 216 of syringe barrel 220 in preparation for dispensing composition 160, as the composition enters channel 212 at this location in order to be dispensed. In one embodiment, the composition may enter one or more holes through a side of hollow handle 204 (e.g., at or near proximal end 206).

As shown in FIGS. 7C and 7D, removable plug 214 is removed so as to unblock delivery channel 212 (FIG. 7C), and then the composition 160 may be dispensed by depressing plunger 158 (FIG. 7D) inserted within syringe barrel 220. As illustrated, once removable plug 214 has been removed, articulating portion 209 may be bent so as to provide a desired dispensing angle. Although illustrated as being dispensed onto a flat surface 170, it will be understood that the composition may be dispensed onto any desired surface (e.g., a tooth). In addition, the distal delivery end 208 may include flocking, fibers, a sponge like tip, or any other application tool head known to those skilled in the art in order to brush or otherwise apply the composition 160.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A mixing device for coupling to and use in mixing a multicomponent composition within a syringe, comprising:

an annular coupling ring for coupling the mixing device to a distal end of a syringe, the coupling ring including a central passageway and providing means for releasably coupling the coupling ring to the distal end of a syringe;

a hollow elongate handle having a proximal end, a distal delivery end, and a delivery channel extending therebetween, the hollow elongate handle being axially slidably disposed through the central passageway of the coupling ring such that the proximal end of the hollow elongate handle can be received through a distal end of a syringe when the coupling ring is coupled thereto during use; and a mixing member disposed at or near the proximal end of the hollow elongate handle such that the mixing member can be axially moved within a syringe by axially sliding the hollow elongate handle relative to the coupling ring so as to mix a composition within a syringe when the coupling ring is coupled to a syringe.

2. A mixing device as recited in claim 1, further comprising a cap that is removably attachable over the distal delivery end of the hollow elongate handle in order to close the distal delivery end.

3. A mixing device as recited in claim 1, further comprising a removable plug disposed within the delivery channel of the hollow elongate handle in order to initially seal the delivery channel.

4. A mixing device as recited in claim 3, wherein the removable plug comprises an elastomer having a shore A durometer hardness not greater than about 40.

5. A mixing device as recited in claim 3, wherein the removable plug comprises a rigid material.

6. A mixing device as recited in claim 5, wherein the rigid material of the removable plug comprises a rigid thermoplastic or a metal.

7. A mixing device as recited in claim 5, wherein the removable plug comprises a lateral bend near a distal end thereof so as to facilitate gripping and selective removal of the plug.

8. A mixing device as recited in claim 3, wherein the removable plug extends through substantially a full length of the hollow elongate handle such that the delivery channel at the proximal end of the hollow elongate handle is also initially closed.

9. A mixing device as recited in claim 1, wherein the mixing member has a substantially circular cross-section, the mixing member further comprising a plurality of channels formed through the substantially circular cross-section so as to define a plurality of outwardly extending paddles between the channels such that the paddles are configured to wipe against an interior side wall of a coupled syringe so as to break up gas bubbles and/or mix a composition so as to be substantially homogenous during use.

10. A mixing device as recited in claim 1, wherein the hollow elongate handle includes an articulating portion near the distal delivery end such that the articulated portion may be angled for more convenient delivery of a mixed composition through the delivery channel.

11. A mixing device as recited in claim 1, wherein the means for releasably coupling the coupling ring to the distal end of a syringe comprises threads or grooves formed in the coupling ring for coupling to complementary threads or grooves formed on the distal end of the syringe.

12. A mixing device as recited in claim 1, wherein the annular coupling ring further comprises a pair of torque wings extending from the annular coupling ring for aiding a user in coupling and uncoupling the annular coupling ring from the distal end of a syringe barrel.

13. A syringe mixing system for in situ mixing of a two-part dental composition, comprising:
- a plunger comprising an elongate stem and a plug at a distal end of the elongate stem;
- a syringe barrel for containing a composition, the syringe barrel having a proximal end and a distal end, the plunger being axially slidably disposed within the syringe barrel;
- a sealing ring attached to the syringe barrel and received at least partially within the distal end of the syringe barrel, the sealing ring including a central passageway;
- a hollow elongate handle having a proximal end, a distal delivery end, and a delivery channel extending therebetween, the hollow elongate handle being slidably disposed through the central passageway of the sealing ring; and
- a mixing member disposed at the proximal end of the hollow elongate handle such that the mixing member is axially movable within the syringe barrel by axially sliding the hollow elongate handle relative to the sealing ring in order to mix a composition contained within the syringe barrel during use.

14. A syringe mixing system as recited in claim 13, wherein the hollow elongate handle further comprises a removable cap over distal delivery end such that the distal delivery end is initially closed.

15. A syringe mixing system as recited in claim 13, wherein the hollow elongate handle further comprises a removable plug disposed within the delivery channel.

16. A syringe mixing system as recited in claim 15, wherein the removable plug comprises an elastomer having a shore A durometer hardness not greater than about 40.

17. A syringe mixing system as recited in claim 15, wherein the removable plug comprises a rigid material.

18. A syringe mixing system as recited in claim 17, wherein the rigid material of the removable plug comprises a rigid thermoplastic or a metal.

19. A syringe mixing system as recited in claim 15, wherein the removable plug extends through substantially a full length of the hollow elongate handle such that both the proximal end and distal end of the hollow elongate handle are initially closed.

20. A syringe mixing system as recited in claim 13, wherein the mixing member has a substantially circular cross-section having a maximum diameter approximately equal to an inner diameter of the syringe barrel, the mixing member further comprising a plurality of channels formed through the substantially circular cross section so as to define a plurality of outwardly extending paddles between the channels such that the paddles are configured to wipe against an interior side wall of the syringe barrel so as to break up gas bubbles and/or mix a composition so as to be substantially homogenous.

21. A syringe-in-syringe mixing system for mixing a two-part dental composition, comprising:
- a first inner plunger comprising an elongate stem and a plug at a distal end of the elongate stem;
- a hollow outer plunger for containing a first component, the hollow outer plunger being configured to slidably receive the first inner plunger therein in sealing engagement, and wherein the hollow outer plunger is initially closed at a distal end;
- a syringe barrel for containing a second component initially separate from the first component, the syringe barrel being configured to slidably receive the hollow outer plunger therein in sealing engagement such that the hollow outer plunger acts as a plunger to the syringe barrel;
- an annular coupling ring or a sealing ring disposed at a distal discharge end of the syringe barrel, the annular coupling ring comprising a central passageway and providing means for releasably coupling the coupling ring to a distal end of the syringe barrel, the sealing ring received at least partially within the distal end of the syringe barrel, and the sealing ring including a central passageway therethrough;
- a hollow elongate handle having a proximal end, a distal delivery end, and a delivery channel therethrough, the hollow elongate handle being slidably disposed through the central passageway of the annular coupling ring or the sealing ring; and
- a mixing member disposed at the proximal end of the hollow handle such that the mixing member is axially movable within the syringe barrel by axially sliding the hollow elongate handle relative to the annular coupling ring or the sealing ring so as to mix first and second components together once a first component is introduced through the initially closed distal end of the hollow inner plunger into the syringe barrel with a second component.

22. A syringe-in-syringe mixing system as recited in claim 21, wherein the hollow elongate handle further comprises a removable plug within the distal delivery end such that the distal delivery end is initially closed.

23. A syringe-in-syringe mixing system as recited in claim 22, wherein the removable plug extends through substantially a full length of the hollow elongate handle such that the proximal end of the hollow elongate handle is also initially closed.

24. A syringe-in-syringe mixing system as recited in claim 22, wherein the removable plug comprises a lateral bend near a distal end thereof so as to facilitate gripping and selective removal of the plug.

25. A syringe-in-syringe mixing system as recited in claim 21, wherein the mixing member has a substantially circular cross-section having a maximum diameter approximately equal to an inner diameter of the syringe barrel, the mixing member further comprising a plurality of channels formed through the substantially circular cross-section so as to define a plurality of outwardly extending paddles between the channels such that the paddles are configured to wipe against an interior side wall of the syringe barrel so as to break up gas bubbles and/or mix two components contained within the syringe barrel homogenously together.

26. A syringe-in-syringe mixing system for mixing a two-part dental composition, comprising:
- a first inner plunger comprising an elongate stem and a plug at a distal end of the elongate stem;
- a hollow outer plunger for containing a first component, the hollow outer plunger being configured to slidably receive the first inner plunger therein in sealing engagement, and wherein the hollow outer plunger is initially closed at a distal end;
- a syringe barrel for containing a second component initially separate from the first component, the syringe barrel being configured to slidably receive the hollow outer plunger therein in sealing engagement such that the hollow outer plunger acts as a plunger to the syringe barrel;
- a hollow elongate handle having a proximal end, a distal delivery end, and a delivery channel therethrough, the hollow elongate handle being slidably disposed through the distal end of the syringe barrel; and
- a mixing member disposed at the proximal end of the hollow handle such that the mixing member is axially movable within the syringe barrel by axially sliding the hollow elongate handle relative to distal end of the syringe barrel so as to mix first and second components together once a first component is introduced through the initially closed distal end of the hollow inner plunger into the syringe barrel with a second component wherein both the syringe barrel and the hollow outer plunger each comprise a proximally disposed flange, further comprising a selectively removable clip having an engagement length that engages around the hollow outer plunger, the engagement length being approximately equal to the length of the hollow outer plunger, the clip being initially clipped around the hollow outer plunger so as to engage between the flanges, preventing the hollow outer plunger from being pressed into the syringe barrel until the first inner plunger is fully inserted into the hollow outer plunger and the clip is removed.

\* \* \* \* \*

UNITED STATES PATENT AND TRADEMARK OFFICE
CERTIFICATE OF CORRECTION

| | | |
|---|---|---|
| PATENT NO. | : 7,879,002 B2 | Page 1 of 1 |
| APPLICATION NO. | : 12/258746 | |
| DATED | : February 1, 2011 | |
| INVENTOR(S) | : Jessop | |

It is certified that error appears in the above-identified patent and that said Letters Patent is hereby corrected as shown below:

Column 3
Line 15, change "end, an axial" to --end, and an axial--

Column 5
Line 2, change "consistency)" to --consistency).--

Column 6
Line 43, change "a through proximal" to --through proximal--

Column 8
Line 8, change "220" to --202--
Line 11, change "Elongate handle 202" to --Elongate handle 204--
Line 30, change "syringe barrel 216" to --syringe barrel 220--
Line 57, change "safety 159 clip" to --safety clip 159--

Column 13
Line 6, change "component" to --component;--

Signed and Sealed this
Fifth Day of July, 2011

David J. Kappos
*Director of the United States Patent and Trademark Office*